United States Patent [19]

Kitamura et al.

[11] Patent Number: 5,403,801
[45] Date of Patent: Apr. 4, 1995

[54] PROCESS FOR PRODUCING ε-CAPROLACTAM AND ACTIVATING SOLID CATALYSTS THEREFOR

[75] Inventors: Masaru Kitamura, Takatsuki; Hiroshi Ichihashi, Ohtsu; Hideto Tojima, Kyoto, all of Japan

[73] Assignee: Sumitomo Chemical Company, Limited, Osaka, Japan

[21] Appl. No.: 10,791

[22] Filed: Jan. 29, 1993

Related U.S. Application Data

[62] Division of Ser. No. 811,627, Dec. 23, 1991, Pat. No. 5,212,302.

[30] Foreign Application Priority Data

Dec. 26, 1990 [JP] Japan ................ 2-406823

[51] Int. Cl.⁶ .................... B01J 37/00; B01J 29/28
[52] U.S. Cl. .................................. 502/86
[58] Field of Search .................. 502/86, 25, 26

[56] References Cited

U.S. PATENT DOCUMENTS

| | | | |
|---|---|---|---|
| 3,523,887 | 8/1970 | Hanson et al. | 502/26 |
| 4,043,938 | 8/1977 | Reif et al. | 502/26 |
| 4,139,433 | 2/1979 | Ward | 502/26 |
| 4,477,582 | 10/1984 | Miale | 502/86 |
| 4,536,485 | 8/1985 | Topp-Jorgensen | 502/86 |
| 4,678,763 | 7/1987 | Chang et al. | 302/26 |
| 4,828,812 | 5/1989 | McCullen et al. | 423/326 |
| 4,837,398 | 6/1989 | Chang et al. | 502/86 |
| 4,863,885 | 9/1989 | Degnan, Jr. | 502/86 |
| 4,871,702 | 10/1989 | Chang et al. | 502/86 |
| 4,912,275 | 3/1990 | Chang et al. | 585/408 |
| 5,057,474 | 10/1991 | Wielers | 502/86 |

FOREIGN PATENT DOCUMENTS

| | | | |
|---|---|---|---|
| 035830 | 9/1981 | European Pat. Off. | 423/326 |
| 134330 | 3/1985 | European Pat. Off. | 502/86 |
| 134850 | 3/1985 | European Pat. Off. | 502/71 |
| 163429 | 12/1985 | European Pat. Off. | 502/86 |
| 169027 | 1/1986 | European Pat. Off. | 502/86 |
| 223396 | 5/1987 | European Pat. Off. | 423/326 |
| 242960 | 10/1987 | European Pat. Off. | 540/536 |
| 251168 | 1/1988 | European Pat. Off. | 540/536 |
| 302636 | 2/1989 | European Pat. Off. | 502/71 |
| 326759 | 8/1989 | European Pat. Off. | 502/71 |
| 380364 | 8/1990 | European Pat. Off. | 540/536 |

*Primary Examiner*—Carl F. Dees
*Attorney, Agent, or Firm*—Cushman, Darby & Cushman

[57] ABSTRACT

In the production of ε-caprolactam from cyclohexanon oxime in gaseous phase in the presence of solid catalysts, the catalysts, no matter whether they may have worked, are brought into contact with either aqueous solution of ammonium salts and at least one basic material or ammonia water.

12 Claims, No Drawings

PROCESS FOR PRODUCING ε-CAPROLACTAM AND ACTIVATING SOLID CATALYSTS THEREFOR

This is a division of application Ser. No. 07/811,627, now U.S. Pat. No. 5,212,302, filed Dec. 23, 1991.

The present invention relates to a process for producing ε-caprolactam from cyclohexanon oxime under gas phase conditions in the presence of solid catalysts and an activation process of the solid catalysts. The activation means to increase activity of brand-new catalysts which have not yet been worked as catalysts and to recover activity of catalysts whose activity has been degraded after the catalysts are used in reactions. ε-caprolactam is a material for producing nylon, etc.

The present inventors proposed a process wherein cyclohexanon oxime is subjected to Beckmann rearrangement under gaseous conditions in the presence of solid catalysts (U.S. Pat. No. 4,968,793). However, it has been desired to have activity of solid catalysts increased or made larger.

One of approaches to increase activity of catalysts in cracking is contacting zeolites with a mixture solvent of alkali metal aluminates and ammonia (EP 134850). Another approach in isomerization of paraffins is contacting titanosilicate with aqueous solution (pH 7–10) of gaseous ammonia or ammonium nitrate (U.S. Pat. No. 4,828,812). Another approach in conversion of methanol to gasoline is ammoniation of zeolites with ammoniac compounds such as ammonia gas, ammonia water and aqueous ammonium nitrate solution, and then heat treatments until ammonia is removed without removal of a hydroxyl group out of zeolites (EP 223396). The other approach in cracking of hydrocarbons is contacting zeolites such as ZSM-12, 20 and 23 with steam, and then cation-exchanging with ammonium salts such as ammonium sulfate (EP 35830).

In addition, solid catalysts usually degrade in their activity according to a period of time worked in reactions. Either regeneration of such degraded catalysts to recover their activity or replacement of brand-new catalysts for degraded ones is compelled. Regeneration is usually carried out by burning carbonaceous materials deposited on catalysts with air or other molecular oxygen-containing gas (Shokubai Kagaku Koza, Vol. 7, Catalytic Reaction (2), Oxidation, Dehydrogenation, Decomposition, —edited by Shokubai Gakkai, 1967, page 278, Chizin Shoin). The present inventors proposed to burn carbonaceous materials with molecular oxygen-containing gas in the presence of alcohols in order to regenerate solid catalysts (JP 2-207454A). Another approach in decomposition of n-hexane is bringing degraded zeolites in contact with water, and then ion-exchanging with ammonium salts such as ammonium nitrate (EP 169027). Another approach in conversion of methanol to hydrocarbons is bringing degraded zeolites in contact with ammonia and steam at a temperature range of 100°–1000° C., except zeolites having $SiO_2/Al_2O_3$ ratio as high as 26000 (EP 134330 and EP 163429). The other approach in cracking and conversion of alcohols to hydrocarbons is contacting degraded zeolites with aqueous ammonia solution, as long as catalysts to be regenerated contain alumina binders (U.S. Pat. No. 4,837,398).

The present inventors have studied increase of brand-new solid catalysts for preparing ε-caprolactam and recovery of activity of degraded solid catalysts to find that the desired result is obtained by contacting solid catalysts with aqueous solution of specific basic materials and ammonium salts or ammonia, no matter what activity of the catalysts may be.

According to the present invention where ε-caprolactam is produced from cyclohexanon oxime under gaseous conditions in the presence of solid catalysts, catalysts defined below are used. That is, catalysts have been subjected to contact with either
1. aqueous solution of ammonium salts and at least one basic material selected from ammonia, lower alkylamines, allylamines and alkylammonium hydroxides, or
2. ammonia water.

Furthermore, according to the present invention, activation of solid catalysts for producing ε-caprolactam is effected by contacting the catalysts with either
1. aqueous solution of ammonium salts and at least one basic material selected from ammonia, lower alkylamines, allylamines and alkylammonium hydroxides, or
2. ammonia water.

Solid catalysts are, for example, silica-alumina and zeolites, preferably zeolites, more preferably crystalline silica and crystalline metallosilicates. Crystalline silica consists substantially of silicon and oxygen. Crystalline metallosilicates have 5 or more, preferably at least 500, of Si/Me atom ratio wherein Me is at least one metal selected from Al, Ga, Fe, B, Zn, Cr, Be, Co, La, Ge, Ti, Zr, Hf, V, Ni, Sb, Bi, Cu and Nb. Si/Me atom ratio is assayed by atomic absorption, fluoroscent X-ray analysis and any other known methods. These crystalline silica or crystalline metallosilicates have various structures, but preferably pentasil structure.

Any methods for producing crystalline silica or crystalline metallosilicates are employed. One of the methods is thoroughly carrying out hydrothermal reaction in autoclaves from silica sources, water, quaternary ammonium and, if necessary, metal sources until crystals appear, calcining the crystals, ion-exchanging with, for example, ammonium salts, drying and, if desired, further calcining.

The present process for improving or increasing activity of brand-new solid catalysts is applied to after the first calcining mentioned above is over. For instance, the process may be applied to the ion-exchanging step with ammonium salts, after the ion-exchanging, or after the drying. Any other applications may be applied. Solid catalysts may be subjected to conventional ion-exchange after the present treatment is applied to.

One of features of the present invention is to increase or make greater activity of solid catalysts by use of aqueous solution of ammonium salts and specific basic materials, or ammonia water.

The basic materials are ammonia, lower alkylamines, allylamines and alkylammonium hydroxides. At least one of them is used.

Lower alkylamines have the formula $$NR_1R_2R_3 \qquad (1)$$

wherein $R_1, R_2$ and $R_3$ each is a hydrogen atom or a lower alkyl group, but $R_1$, $R_2$ and $R_3$ all are not hydrogens. $R_1$, $R_2$ and $R_3$ are lower alkyl ($C_{1-4}$) groups, i.e., methyl, ethyl, propyl and butyl. The alkylamines are $C_{1-12}$ alkylamines, for example, monomethylamine, monoethylamine, monopropylamine, monobutylamine, dimethylamine, diethylamine, dipropylamine, dibutylamine, trimethylamine, triethylamine, tripropylamine and tributylamine.

Allylamines are $C_{3-9}$ allylamines such as monoallylamine, diallylamine and triallylamine.

Alkylammonium hydroxides have the formula:

$$R_4R_5R_6R_7N^+OH^- \qquad (2)$$

wherein $R_4$, $R_5$, $R_6$ and $R_7$ each is a hydrogen atom, a lower alkyl group, an aralkyl group, an aryl group or an allyl group but $R_4$, $R_5$, $R_6$ and $R_7$ all are not hydrogens. $R_4$, $R_5$, $R_6$ and $R_7$ may be lower alkyl ($C_{1-4}$) groups such as methyl, ethyl, propyl and butyl; aralkyl ($C_{7-8}$) groups such as benzyl and tolylmethyl; aryl groups ($C_{6-7}$) such as phenyl and tolyl; and an allyl group. The alkylammonium hydroxides are $C_{1-20}$ alkylammonium hydroxides, for example, tetramethylammonium hydroxide, tetraethylammonium hydroxide, tetrapropylammonium hydroxide, tetrabutylammonium hydroxide, tributylbenzylammonium hydroxide, di-p-tolylammonium hydroxide, di-m-tolylammonium hydroxide, di-o-tolylammonium hydroxide, diphenylammonium hydroxide, mono-p-tolylammonium hydroxide, mono-m-tolylammonium hydroxide, mono-o-tolylammonium hydroxide, monophenylammonium hydroxide, tetraallylammonium hydroxide, trimethylammonium hydroxide, dimethylammonium hydroxide, monomethylammonium hydroxide, triethylammonium hydroxide, diethylammonium hydroxide, monoethylammonium hydroxide, tripropylammonium hydroxide, dipropylammonium hydroxide, monopropylammonium hydroxide, tributylammonium hydroxide, dibutylammonium hydroxide and monobutylammonium hydroxide.

Quaternary ammonium salts, e.g., alkylammonium bromides or chlorides may be used in place of the alkylammonium hydroxides, when ammonia, lower alkylamines or allylamines are used together.

Ammonium salts are, for example, ammonium chloride, ammonium sulfate and ammonium nitrate.

Mixing ratio of basic materials such as ammonia and ammonium salts is determined by pH.

The present activation is carried out in the pH range of 9 or more, preferably 9-13. Temperature is in the range of 30°-200° C., usually 60°-100° C. A period of time is usually within the range of 0.05-10 hours. The treatment may be repeated a few times, if necessary. After the treatment is over, washing with water may be made. Alternatively, washing with acids such as hydrochloric acid may be made before washing with water is effected.

The present activation is also able to apply in order to recover activity of degraded catalysts, by applying the same treatment solution as above, i.e., aqueous solution of ammonium salts and at least one basic material selected from ammonia, lower alkylamines, allylamines and alkylammonium hydroxides, or ammonia water. The degraded catalysts include catalysts whose activity is decreased after they worked in, for example, rearrangement of cyclohexanon oxime under gaseous phases, or those damaged by heat.

It is desirable to be subjected to a pretreatment for removal of carbonaceous materials deposited on degraded catalysts, such as contact with air or other molecular oxygen-containing gas with or without alcohols, before the present activation step is applied to degraded catalysts.

It is another feature of the present activation to recover activity of degraded catalysts by use of aqueous solution of ammonium salts and specific basic materials, or ammonia water. It is the other feature to recover activity of degraded catalysts by use of ammonia gas.

The activation with ammonia gas may be carried out by accompanying inert gas such as nitrogen gas and steam. Feeding speed of ammonia gas is not critical but usually in the range of 1–2000 liter/hr/kg of catalysts. A period of time varies depending on degradation degree, but usually is within the range of 1–100 hours. Temperature is preferably 250° C. or lower, more preferably in the range of 100°-200° C. Pressure is usually 10 atm or lower.

Any embodiment of the present activation is applied to, as long as catalysts are thoroughly in contact with aqueous solution of basic materials and ammonium salts, or ammonia. One of embodiments is that catalysts are charged in reactors and aqueous solution of basic materials and ammonium salts, or ammonia is fed in the reactors until the catalysts are dipped under stirring. Alternatively, the aqueous solution as above or ammonia is passed through a column in which catalysts have been packed.

The present invention is explained referring to production of $\epsilon$-caprolactam.

The present invention is carried out by vapor phase contacting reaction in a fixed bed system or a fluidized bed system. Temperature is usually within the range of 250°-500° C. Reaction speed is not large and selectivity of $\epsilon$-caprolactam becomes small when the temperature is below 250° C. Selectivity of $\epsilon$-caprolactam becomes small when the temperature is higher than 500° C. Preferable range is 300°-450° C., more preferably 300°-400° C. Pressure is not critical but usually in the range of 0.05–10 kg/cm$_2$.

Space velocity of cyclohexanon oxime is usually within the range of 0.1–40 hr$^{-1}$ in terms of WHSV, i.e., 0.1–40 kg/hr of cyclohexanon oxime per kg of catalysts. Preferable range is 0.2–20 hr$^{-1}$, more preferably 0.5–10 hr$^{-1}$, in terms of WHSV.

Separation of $\epsilon$-caprolactam from reaction mixtures is carried out by any known methods. One of the methods is cooling gas obtained after the reaction above is over until condensation is effected, extracting and then distilling or crystallization, until $\epsilon$-caprolactam is obtained.

As explained above, activity of solid catalysts is improved by contacting with aqueous solution of specific basic materials and ammonium salts, or ammonia. Activity of degraded catalysts is also recovered and life of the catalysts is elongated by the same treatment as above. Production of $\epsilon$-caprolactam is carried out with high efficiency when solid catalysts having improved activity or activity recovered are employed.

EXAMPLES

Reference Example 1

(Preparation of solid A)

Tetraethylorthosilicate, Si(OC$_2$H$_5$)$_4$, (Al=lower than 10 ppm) 500 g, 10% aqueous tetra-n-propylammonium hydroxide solution (1120 g) and ethanol (1070 g) charged in an autoclave (5 liter) made of stainless steel are stirred vigorously for 120 min. PH of the solution is 13. After a cover of the autoclave is tightened, it is dipped in an oil bath. While inner temperature is kept at 105° C., hydrothermal reaction is conducted under stirring (400 rpm or more) for 96 hours. Pressure in the autoclave reaches 2-3 kg/cm$^2$. PH of the solution is 11.8 after the reaction is over.

After white solid is filtered, washing of the solid with distilled water is continued until pH of filtrate reaches about 7. Crystals obtained are dried at 120° C. for 16 hours and then calcined at a temperature within the range of 500°–530° C. for 4 hours in the stream of air to obtain powdery white crystals (130 g) which are identified as pentasil zeolite by power X-ray diffraction assay. Atomic absorption spectroscopy assay gives 3 ppm of Al contained. This white crystals are referred to as solid A (catalyst precursor).

Reference Example 2

(Preparation of solid B)

Aqueous tetra-n-propylammonium hydroxide solution (10%, 232.86 g), ethanol (62.33 g), distilled water (50.4 g), aqueous solution (2 ml) containing titanium tetraisopropoxide (0.025 g) and tetraethylorthosilicate, $Si(OC_2H_5)_4$, (104.17 g) charged in this order in an autoclave (1.5 liter) made of stainless steel are thoroughly stirred for one hour. While inner temperature is kept at 105° C., hydrothermal reaction is carried out under stirring (400 rpm or more) for 96 hours. After white solid is filtered, washing with distilled water is continued until pH of filtrate reaches about 7. Crystals obtained are dried at 120° C. for 16 hours, and calcined at 500°–550° C. for 4 hours in the stream of air, to obtain white powder crystals (27 g). The crystals are identified as titanosilicate having similar structure to pentasil zeolite by powder X-ray diffraction. Atomic absorption spectroscopy assay gives 9600 of Si/Ti atom ratio. This white crystals are referred to as solid B (catalyst precursor).

Example 1

Improvement in catalytic activity

To the solid A prepared by reference example 1 and charged in an autoclave is added a mixture (pH 11.5, 50 g) of aqueous ammonium nitrate solution (7.5 wt %, 20 g) and aqueous ammonia solution (28 wt %, 30 g). The content is kept for one hour under stirring at 90° C. Solid obtained after filtration is charged again in the autoclave and the same procedure as above is repeated three times. Solid is filtered, washed with water and dried. Solid thus obtained is named as catalyst C.

Production of ε-caprolactam (1) A tube (1 cm inner diameter) made of silica glass in which the catalyst C (0.375 g, 0.6 ml) shaped under pressure and sieved at 24–48 mesh has been packed, is pre-heated at 350° C. for one hour under a nitrogen stream (4.2 liter/hr). A mixture of cyclohexanon oxime/methanol (1/1.8 by weight) is charged to the column under 8.4 g/hr. WHSV=8 hr$^{-1}$. Temperature of a catalyst layer is kept at 350° C. Reaction is conducted for 6.25 hours. Reaction product is collected every one hour under ice cooling and assayed by gas chromatography.

WHSV (hr$^{-1}$)=O/C

Conversion of cyclohexanon oxime (%)=(X−Y)/X×100

Selectivity of ε-caprolactam (%)=Z/(X−Y)×100 wherein

O=charging speed of cyclohexanon oxime (kg/hr)
C=catalyst weight (kg)
X=cyclohexanon oxime charged (mol)
Y=unaltered cyclohexanon oxime (mol)
Z=ε-caprolactam in product (mol)

(2) After the reaction is over, charging of solution of cyclohexanon oxime in methanol is stopped. A mixture of nitrogen gas (2.5 liter/hr) and air (2.5 liter/hr) is bubbled in methanol (0° C.) and methanol (3.8 vol %, 0° C. saturated concentration) is vaporized in and accompanied by nitrogen/air mixture gas before being charged in the tube. Temperature of the catalyst layer is increased to 430° C. and the charging is conducted for 23 hours, in order to remove carbonaceous materials deposited on the catalysts.

(3) Temperature was lowered to 350° C. while nitrogen gas (4.2 liter/hr) is charged. The same reaction procedure as in (1) is repeated.

(4) After the reaction (1) is over, the same procedure for removal of carbonaceous materials as in (2) is applied to.

A run wherein the reaction (1) and removal of carbonaceous materials (2) are involved is repeated 30 times in the total. Results are shown in Table 1.

TABLE 1

| Run No. | Reaction time elapsed (hr) | | | | | |
|---|---|---|---|---|---|---|
| | 1.25 | 2.25 | 3.25 | 4.25 | 5.25 | 6.25 |
| 1 Con. | 99.8 | 99.6 | 99.6 | 99.5 | 99.5 | 99.5 |
| Sel. | 96.6 | 96.0 | 94.8 | 96.4 | 96.4 | 96.5 |
| 2 Con. | 99.8 | 99.6 | 99.6 | 99.5 | 99.5 | 99.5 |
| Sel. | 96.0 | 95.9 | 95.1 | 95.7 | 96.2 | 95.1 |
| 10 Con. | 99.6 | 99.5 | 99.4 | 99.3 | 99.3 | 99.3 |
| Sel. | 95.1 | 96.7 | 95.3 | 96.7 | 96.3 | 95.4 |
| 20 Con. | 97.4 | 96.8 | 96.4 | 96.0 | 95.8 | 95.5 |
| Sel. | 96.7 | 95.8 | 94.9 | 95.4 | 95.5 | 95.0 |
| 30 Con. | 97.6 | 96.7 | 96.5 | 96.0 | 95.7 | 95.3 |
| Sel. | 96.9 | 95.7 | 95.1 | 94.4 | 94.7 | 95.3 |

Notes
Con. = conversion (%)
Sel. = selectivity (%)
The same hereinafter.

Comparative Example 1

A mixture of the solid A (5 g) and aqueous ammonium nitrate solution (7.5 wt %, 50 g) is subjected to an ion-exchange treatment at 90° C. for one hour, and is filtered. The ion-exchange treatment is effected three times. Then, the product is washed with distilled water and dried. The product is referred to as catalyst D.

Production of caprolactam and removal of carbonaceous materials are repeated 30 times in the same manner as in Example 1 using the catalyst D. The results are shown in Table 2.

TABLE 2

| Run No. | Reaction time elapsed (hr) | | | | | |
|---|---|---|---|---|---|---|
| | 1.25 | 2.25 | 3.25 | 4.25 | 5.25 | 6.25 |
| 1 Con. | 99.4 | 99.1 | 98.7 | 98.5 | 98.2 | 98.0 |
| Sel. | 95.1 | 96.0 | 95.2 | 96.5 | 95.5 | 95.1 |
| 2 Con. | 98.0 | 97.9 | 97.6 | 97.3 | 97.1 | 97.0 |
| Sel. | 96.5 | 95.3 | 95.1 | 96.8 | 96.5 | 96.6 |
| 10 Con. | 94.3 | 92.7 | 90.6 | 89.1 | 88.4 | 87.6 |
| Sel. | 95.3 | 94.7 | 95.1 | 95.6 | 94.8 | 94.2 |
| 20 Con. | 88.3 | 84.3 | 80.6 | 78.1 | 75.9 | 74.3 |
| Sel. | 95.6 | 92.7 | 93.5 | 94.2 | 94.6 | 94.5 |
| 30 Con. | 82.4 | 77.6 | 74.3 | 70.3 | 67.4 | 64.2 |
| Sel. | 94.3 | 94.8 | 92.0 | 93.1 | 92.8 | 92.5 |

Example 2

Improvement in catalytic activity

Solid B (5 g) prepared by Reference example 2 is packed in an autoclave and is treated as in Example 1, i.e., improvement in catalytic activity. The solid obtained is referred to as catalyst E.

Production of ε-caprolactam

Example 1, i.e., the steps (1) and (2) mentioned therein, is repeated 20 times except that the catalyst E is used in place of the catalyst A. Table 3 shows the results.

TABLE 3

| Run No. | | Reaction time elapsed (hr) | | | | |
|---|---|---|---|---|---|---|
| | | 1.25 | 2.25 | 3.25 | 4.25 | 5.25 | 6.25 |
| 1 | Con. | 99.5 | 99.3 | 99.1 | 98.9 | 98.8 | 98.6 |
| | Sel. | 96.0 | 96.0 | 97.2 | 96.7 | 96.7 | 96.8 |
| 2 | Con. | 99.9 | 99.8 | 99.8 | 99.8 | 99.8 | 99.8 |
| | Sel. | 95.9 | 96.1 | 96.0 | 96.2 | 96.0 | 96.6 |
| 10 | Con. | 99.8 | 99.6 | 99.8 | 99.7 | 99.6 | 99.9 |
| | Sel. | 96.5 | 96.6 | 96.6 | 96.5 | 95.4 | 96.7 |
| 20 | Con. | 99.9 | 99.8 | 99.9 | 99.6 | 99.5 | 99.8 |
| | Sel. | 96.3 | 95.7 | 96.8 | 96.0 | 96.1 | 96.8 |

Example 3

Improvement in catalytic activity

Solid A (5 g) prepared by Reference example 1 is charged in an autoclave and ammonia water (pH=11.5, 50 g) is added. The mixture is left to stand for 10 min. at 90° C. under stirring. Solid is filtered and charged again in the autoclave. The same procedure as above is repeated six times. The solid is filtered, washed with water and dried. The solid is referred to as Catalyst G.

Production of ε-caprolactam

Catalyst G (0.25 g, 0.4 ml) shaped under pressure, sieved at 24–48 mesh and packed in a reaction tube (1 cm inner diameter) made of silica glass is pre-heated for one hour at a temperature of 350° C. in the nitrogen stream (4.2 liter/hr). Cyclohexanon oxime/methanol (1/1.8 by weight, 11.8 g/hr) is fed to the reaction tube. WHSV=16.8 hr$^{-1}$. Temperature of the catalyst layer is 350° C. The reaction is effected for 10.25 hrs. Product is collected every one hour under ice cooling and assayed by gas-chromatography. The results are shown in Table 4.

TABLE 4

| | Reaction time elapsed (hr) | | |
|---|---|---|---|
| | 1.25 | 5.25 | 10.25 |
| Con. | 85.1 | 73.5 | 67.9 |
| Sel. | 88.8 | 88.7 | 88.3 |

Example 4

Production of ε-caprolactam is carried out in the same manner as in Example 3 using the catalyst C prepared by Example 1. The results are shown in Table 5.

TABLE 5

| | Reaction time elapsed (hr) | | |
|---|---|---|---|
| | 1.25 | 5.25 | 10.25 |
| Con. | 96.1 | 89.7 | 85.4 |
| Sel. | 89.4 | 88.6 | 88.5 |

Example 5

Improvement in catalytic activity

To the solid A (5 g) prepared by Reference example 1 and charged in an autoclave is added a mixture solution (pH=12, 50 g) of aqueous ammonium sulfate (14 wt %, 20 g) and ammonia water (28 wt %, 30 g). The mixture is left to stand for one hour at 90° C. under stirring. After filtration, solid is again charged in the autoclave. The same procedure as above is repeated three times. The solid is filtered, washed with water and dried. The solid obtained is referred to as catalyst H.

Production of ε-caprolactam

Example 3 is repeated except that the catalyst H is used in place of the catalyst G. The results are shown in Table 6.

TABLE 6

| | Reaction time elapsed (hr) | | |
|---|---|---|---|
| | 1.25 | 5.25 | 10.25 |
| Con. | 91.2 | 73.1 | 65.4 |
| Sel. | 91.2 | 90.1 | 88.0 |

Example 6

Improvement in catalytic activity

To the solid (5 g) prepared by Reference example 1 and charged in an autoclave is added a mixture solution (pH=9.5, 50 g) of aqueous ammonium nitrate solution (7.5 wt %, 49 g) and ammonia water (28 wt %, 1 g). The mixture is left to stand for one hour at a temperature of 90° C. under stirring. After filtration, solid is again charged in the autoclave. The same procedure as above is repeated three times. The solid is filtered, washed with water and dried. The solid is referred to as catalyst I.

Production of ε-caprolactam

Example 3 is repeated except that the catalyst I is used in place of the catalyst G. The results are shown in Table 7.

TABLE 7

| | Reaction time elapsed (hr) | | |
|---|---|---|---|
| | 1.25 | 5.25 | 10.25 |
| Con. | 85.2 | 73.2 | 66.2 |
| Sel. | 89.5 | 90.1 | 89.5 |

Example 7

Improvement in catalytic activity

To the solid A (5 g) prepared by Reference example 1 and charged in an autoclave is added a mixture solution (pH=11, 50 g) of aqueous ammonium nitrate solution (7.5 wt %, 32 g) and aqueous trimethylamine solution (about 30 wt %, 18 g). The mixture is left to stand for one hour at a temperature of 90° C. under stirring. After filtration, solid is again charged in the autoclave. The same procedure as above is repeated three times. The solid is filtered, washed with water and dried. The solid is referred to as catalyst J.

Production of ε-caprolactam

Example 3 is repeated except that the catalyst J is used in place of the catalyst G. The results are shown in Table 8.

TABLE 8

| | Reaction time elapsed (hr) | | |
|---|---|---|---|
| | 1.25 | 5.25 | 10.25 |
| Con. | 86.2 | 76.5 | 68.5 |
| Sel. | 86.9 | 88.3 | 87.8 |

Example 8

Improvement in catalytic activity

To the solid A (5 g) prepared by Reference example 1 and charged in an autoclave is added a mixture solution (pH=10, 50 g) of aqueous ammonium nitrate solution (7.5 wt %, 19 g) and aqueous tetra-n-propylammonium solution (10 wt %, 31 g). The mixture is left to stand for one hour at a temperature of 90° C. under stirring. After filtration, solid is again charged in the autoclave. The same procedure as above is repeated three times. The solid is filtered, washed with water and dried. The solid is referred to catalyst K.

Production of ε-caprolactam

Example 3 is repeated except that the catalyst K is used in place of the catalyst G. The results are shown in Table 9.

TABLE 9

| | Reaction time elapsed (hr) | | |
|---|---|---|---|
| | 1.25 | 5.25 | 10.25 |
| Con. | 87.1 | 70.9 | 65.4 |
| Sel. | 89.8 | 89.5 | 89.4 |

Comparative Example 2

Example 3 is repeated except that a catalyst prepared in the same manner as the catalyst D obtained in Comparative example 1, to prepare ε-caprolactam. The results are shown in Table 10.

TABLE 10

| | Reaction time elapsed (hr) | | |
|---|---|---|---|
| | 1.25 | 5.25 | 10.25 |
| Con. | 91.1 | 69.4 | 55.6 |
| Sel. | 89.4 | 89.5 | 90.0 |

Example 9

Improvement in catalytic activity

To a catalyst (2 g) prepared in the same manner as the catalyst G in Example 3 is added aqueous ammonium nitrate solution (7.5 wt %, 20 g). The mixture is subjected to an ion-exchange treatment for one hour at a temperature of 90° C. After filtration, the same procedure as above is repeated three times. The solid is washed with distilled water and dried. The solid is referred to as Catalyst L.

Production of ε-caprolactam

Example 3 is repeated except that the catalyst L is used in place of the catalyst G. The results are shown in Table 11.

TABLE 11

| | Reaction time elapsed (hr) | | |
|---|---|---|---|
| | 1.25 | 5.25 | 10.25 |
| Con. | 87.4 | 72.5 | 65.0 |
| Sel. | 88.8 | 90.8 | 89.6 |

Reference example 3
(Preparation of catalyst M)

A mixture of tetraethylorthosilicate, $Si(OC_2H_5)_4$, (Al=less than 10 ppm) 100 g, 10% aqueous tetra-n-propylammonium hydroxide solution (224.0 g) and ethanol (214 g) in an autoclave (1.5 liter) made of stainless steel is stirred vigorously for 30 min. pH of the solution is 13. After a cover of the autoclave is tightened, it is dipped in an oil bath. Hydrothermal reaction is carried out for 96 hours under stirring (400 rpm or more), keeping inner temperature at 105° C. Pressure reaches 2–3 kg/cm$_2$. PH at the end of the reaction is 11.8. White solid crystals are filtered and continuously washed with distilled water until filtrate has pH of about 7. The crystals are dried at a temperature of 120° C. for 16 hours, and then calcined at a temperature of 530° C. for four hours in a stream of air until powder white crystals (27 g) are obtained. The crystals are identified as pentasil zeolite by powder X-ray diffraction. Atomic absorption spectroscopy assay gives 3 ppm of Al content.

To the crystals (10 g) is added 5% aqueous ammonium chloride solution (100 g). The mixture is subjected to an ion-exchange treatment for one hour at a temperature within the range of 50°–60° C. and filtered. The same ion-exchange treatment is repeated four times. The crystals obtained are washed with distilled water until Cl$^-$ ion is free. The crystals are dried and shaped under pressure and sieved at 24–48 mesh. The crystals are calcined at a temperature of 500° C. for one hour in a stream of nitrogen to obtain a catalyst which is referred to as catalyst M.

Reference Example 4
(Preparation of catalyst N)

Aqueous tetra-n-propylammonium hydroxide solution (10 %, 232.86 g), ethanol (62.33 g), distilled water (50.49 g), aqueous solution (2 ml) containing titanium tetraisopropoxide (0.071 g) and tetraethylorthosilicate, $Si(OC_2H_5)_4$ (104.17 g) are charged in this order in an autoclave (1.5 liter) made of stainless steel. The content is stirred thoroughly for one hour. Hydrothermal reaction is effected for 96 hours under stirring (400 rpm or more), keeping inner temperature at 105° C. White solid obtained is filtered and continuously washed with distilled water until filtrate has pH of about 7. The solid is dried at a temperature of 120° C. for 16 hours. The solid is calcined at a temperature of 530° C. for four hours in an air stream to obtain white powder crystals (27 g), which are identified as titanosilicate having the similar structure to pentasil zeolite by powder X-ray diffraction. Atomic absorption spectroscopy assay gives 1900 of Si/Ti atom ratio. The crystals are subjected to the same ion-exchange treatment and calcined as in Reference example 1 to obtain a catalyst which is referred to as catalyst N.

Reference Example 5
(Preparation of catalyst O)

A mixture of tetraethylorthosilicate, $Si(OC_2H_5)_4$, (100 g), 10% aqueous tetra-n-propylammonium hydroxide solution (224.0 g) and ethanol (60 g) in an autoclave (1.5 liter) made of stainless steel is thoroughly stirred. To the mixture is added aqueous aluminium sulfate solution (48 g) prepared from $Al_2(SO_4)_3.18H_2O$ (3 g)/water (48 g), and the mixture is vigorously stirred for 30 min. PH of the solution is 13. After a cover of the autoclave is tightened, it is dipped in an oil bath. Hydrothermal reaction is carried out for 120 hours under stirring (400 rpm or more), keeping inner temperature at 105° C. Pressure reaches 2–3 kg/cm$^2$. PH at the end of the reaction is 11.8. White solid crystals are treated as in Reference example 1 to obtain powder white crystals. The crystals are identified as pentasil zeolite by powder X-ray diffraction. Atomic absorption spectroscopy assay gives 50 of Si/Al atom ratio.

The crystals are subjected to an ion-exchange treatment and calcined in the same manner as in Reference example 3 to obtain a catalyst which is referred to as catalyst O.

Example 10

Production of ε-caprolactam (1) The catalyst M (0.375 g, 0.6 ml) prepared by Reference example 3 and packed in a reaction tube (1 cm inner diameter) made of silica glass is pre-heated at a temperature of 350° C. for one hour in a nitrogen stream (4.2 liter/hr). A mixture of cyclohexanon oxime/methanol (1/1.8 by weight) is charged at speed of 8.4 g/hr under WHSV=8 hr$^{-1}$ at a catalyst layer temperature of 350° C. for 6.25 hours. Product is collected every one hour under ice cooling and assayed by gas chromatography.

(2) After the reaction is over, no further feeding of cyclohexanon oxime/methanol is made. A mixture of nitrogen gas (2.5 liter/hr) and air (2.5 liter/hr) is bubbled in methanol (0° C.) until methanol (3.8 vol %, 0° C. saturated concentration) is vaporized in and accompanied by nitrogen/air mixture gas. The gas is charged to the reaction tube. Temperature of the catalyst layer is raised to 430° C. The operation is conducted for 23 hours in order to remove carbonaceous materials deposited on the catalyst.

(3) Temperature is lowered to 350° C. while nitrogen is fed (4.2 liter/hr). Then, the step (1) is repeated.

(4) After the reaction is over, the step (2) above is applied to in order to remove carbonaceous materials deposited on the catalyst.

The steps (1) and (2) are conducted in series 20 times. The results are shown in Table 12.

Recovery of catalytic activity

Degraded catalyst (0.375 g) after the 20th removal of carbonaceous materials is over is charged in an autoclave. The catalyst is left to stand at a temperature of 90° C. for one hour in a mixture of ammonia water (28% by wt, 50 ml) and ammonium chloride (4 g). After filtration, solid is transferred to a flask to which HCl (5N, 50 ml) is added. Stirring is made at a temperature of 90° C. for one hour. The solid is filtered, washed with water and dried to obtain a regenerated catalyst.

The dried, regenerated catalyst (0.350 g) is charged in the same reaction tube as above and then the steps (1) and (2) above are repeatedly applied to. The results are shown in Table 13.

TABLE 12

| Run No. | Reaction time elapsed (hr) | | | | | |
|---|---|---|---|---|---|---|
| | 1.25 | 2.25 | 3.25 | 4.25 | 5.25 | 6.25 |
| 1 Con. | 98.8 | 98.1 | 97.2 | 96.9 | 95.9 | 94.7 |
| Sel. | 96.6 | 95.2 | 95.1 | 95.3 | 93.5 | 96.4 |
| 2 Con. | 97.2 | 96.1 | 95.1 | 94.3 | 93.4 | 93.1 |
| Sel. | 96.1 | 96.0 | 95.9 | 95.9 | 95.9 | 95.6 |
| 19 Con. | 93.4 | 86.6 | 82.9 | 80.0 | 78.0 | 75.7 |
| Sel. | 93.8 | 93.2 | 93.8 | 93.2 | 93.2 | 92.9 |
| 20 Con. | 85.8 | 75.2 | 73.6 | 68.3 | 65.3 | 62.8 |
| Sel. | 92.5 | 91.9 | 91.6 | 91.8 | 91.7 | 91.6 |

TABLE 13

| Run No. | Reaction time elapsed (hr) | | | | | |
|---|---|---|---|---|---|---|
| | 1.25 | 2.25 | 3.25 | 4.25 | 5.25 | 6.25 |
| 1 Con. | 95.0 | 93.9 | 92.7 | 91.4 | 90.2 | 89.1 |
| (21) Sel. | 94.5 | 95.2 | 96.0 | 95.9 | 96.0 | 96.0 |
| 2 Con. | 95.9 | 94.3 | 93.1 | 92.1 | 91.2 | 90.2 |
| (22) Sel. | 95.9 | 96.3 | 96.1 | 95.6 | 96.3 | 96.5 |
| 10 Con. | 93.1 | 90.3 | 88.2 | 86.5 | 85.1 | 83.7 |
| (30) Sel. | 92.3 | 94.0 | 94.3 | 94.4 | 94.1 | 94.1 |

Note: Number in parenthesis: Run number serial after Table 12.

Example 11

Production of ε-caprolactam

A catalyst is again prepared as in the same manner as the catalyst M of Reference example 3, in order to confirm whether or not preparation of catalyst and Beckmann rearrangement of cyclohexanon oxime are able to repeat. The catalyst is referred to catalyst M* which contains Al (3 ppm).

The catalyst M* (0.375 g, 0.6 ml) is charged in the same reaction tube as in Example 10. Beckmann rearrangement of cyclohexanon oxime and removal of carbonaceous materials are repeated as in the same manner as in Example 10, except that the step (1), i.e., rearrangement reaction, is effected for one hour in place of 6.25 hours and the step (2), i.e., removal of carbonaceous materials, is effected for three hours in place of 23 hours. The results are shown in Table 14.

Recovery of catalytic activity

Degraded catalyst from which carbonaceous materials have been removed is taken out from the reaction tube and the same regeneration treatment as in Example 10 is applied to.

Beckmann rearrangement of cyclohexanon oxime and removal of carbonaceous materials are repeatedly effected in the same manner as above using the regenerated catalyst. The results are shown in Table 15.

TABLE 14

| Run No. | Results |
|---|---|
| 1 Con. | 98.4 |
| Sel. | 96.8 |
| 2 Con. | 97.1 |
| Sel. | 96.6 |
| 125 Con. | 71.5 |
| Sel. | 91.8 |

TABLE 15

| Run No. | Results |
|---|---|
| 1 Con. | 96.4 |
| (126) Sel. | 96.0 |
| 2 Con. | 95.6 |
| (127) Sel. | 96.5 |
| 80 Con. | 89.4 |
| (205) Sel. | 93.6 |

Note: Number in parenthesis: Run number serial after Table 14.

Example 12

Production of ε-caprolactam

The catalyst N (0.375 g, 0.6 ml) prepared by Reference example 4 is charged in the same reaction tube as in Example 10. Beckmann rearrangement of cyclohexanon oxime and removal of carbonaceous materials are repeatedly effected as in the same manner as in Example 10. The results are shown in Table 16.

Recovery of catalytic activity

Degraded catalyst after carbonaceous materials have been removed is taken out from the reaction tube. In an autoclave, the catalyst (0.375 g) is left to stand with ammonia water (28 wt %, 50 ml) and ammonium chloride (4 g) at a temperature of 90° C. for one hour. After regeneration is over, solid is filtered and charged again in the autoclave as above. The same regeneration as above is repeated three times. The solid is filtered, washed with water and dried.

The catalyst thus obtained (0.350 g) is charged in the same reaction tube as above. Beckmann rearrangement of cyclohexanon oxime and removal of carbonaceous materials are repeated as in the same manner as in Example 10. The results are shown in Table 17.

TABLE 16

| Run No. | | Reaction time elapsed (hr) | | | | | |
|---|---|---|---|---|---|---|---|
| | | 1.25 | 2.25 | 3.25 | 4.25 | 5.25 | 6.25 |
| 1 | Con. | 98.5 | 97.4 | 97.3 | 96.7 | 96.2 | 95.7 |
| | Sel. | 95.6 | 92.5 | 94.1 | 93.4 | 91.3 | 92.0 |
| 2 | Con. | 97.5 | 96.6 | 96.1 | 94.4 | 94.1 | 93.6 |
| | Sel. | 88.0 | 93.5 | 95.6 | 95.1 | 95.6 | 94.2 |
| 19 | Con. | 85.0 | 75.7 | 71.5 | 68.2 | 64.9 | 62.7 |
| | Sel. | 94.8 | 91.4 | 95.1 | 94.2 | 94.1 | 96.5 |
| 20 | Con. | 82.0 | 72.5 | 66.9 | 65.4 | 62.8 | 60.3 |
| | Sel. | 93.2 | 92.6 | 92.7 | 90.6 | 91.2 | 91.7 |

TABLE 17

| Run No. | | Reaction time elapsed (hr) | | | | | |
|---|---|---|---|---|---|---|---|
| | | 1.25 | 2.25 | 3.25 | 4.25 | 5.25 | 6.25 |
| 1 | Con. | 97.2 | 90.0 | 87.8 | 86.7 | 85.9 | 84.1 |
| (21) | Sel. | 88.9 | 89.9 | 91.7 | 94.6 | 93.9 | 93.7 |
| 2 | Con. | 92.9 | 90.7 | 89.8 | 88.8 | 87.9 | 87.0 |
| (22) | Sel. | 93.3 | 92.3 | 92.6 | 94.1 | 95.6 | 94.3 |
| 10 | Con. | 90.3 | 87.6 | 86.4 | 84.9 | 84.7 | 83.6 |
| (30) | Sel. | 93.2 | 95.1 | 92.7 | 94.8 | 87.4 | 86.7 |

Note: Number in parenthesis: Run number serial after Table 16.

Example 13

Enforced degradation of catalysts under high temperature and reaction

In a reaction tube (1 cm inner diameter) made of silica glass is packed with the catalyst M (0.375 g) prepared by Reference example 3. Nitrogen gas (2.5 liter/hr) is bubbled in distilled water (0° C.) until water (0.6 vol %, 0° C. saturated concentration) is vaporized in and accompanied by the nitrogen gas. The gas is charged in the reaction tube at a temperature of 900° C. for two hours, before the-temperature is lowered to room temperature (20° C.).

Beckmann rearrangement of cyclohexanon oxime is carried out in the same manner as in Example 10 in the presence of the catalyst (0.375 g) which has been subjected to the above enforced degradation treatment. The results are shown in Table 18.

Carbonaceous materials deposited on the catalyst are removed by combustion in the same manner as in Example 10.

Recovery of catalytic activity

Degraded catalyst (0.375 g) after carbonaceous materials are removed is charged in an autoclave. The catalyst is left to stand in the autoclave with ammonia water (pH 11.5, 50 ml) at a temperature of 90° C. for one hour. After the catalyst is filtered, the catalyst is again charged in the autoclave and the above procedure was repeated four times. Then, the catalyst is filtered, washed with water and dried.

Beckmann rearrangement of cyclohexanon oxime is carried out in the same manner as above in the presence of the regenerated catalyst. The results are shown in Table 19.

TABLE 18

| Run No. | | Reaction time elapsed (hr) | | | | | |
|---|---|---|---|---|---|---|---|
| | | 1.25 | 2.25 | 3.25 | 4.25 | 5.25 | 6.25 |
| 1 | Con. | 96.6 | 92.8 | 87.5 | 81.9 | 77.0 | 75.9 |
| | Sel. | 92.7 | 92.8 | 94.1 | 94.4 | 95.6 | 94.6 |

TABLE 19

| Run No. | | Reaction time elapsed (hr) | | | | | |
|---|---|---|---|---|---|---|---|
| | | 1.25 | 2.25 | 3.25 | 4.25 | 5.25 | 6.25 |
| 1 | Con. | 99.8 | 99.6 | 99.3 | 99.2 | 99.0 | 99.4 |
| | Sel. | 93.2 | 92.6 | 94.2 | 92.6 | 93.0 | 93.5 |

Example 14

Enforced degradation of catalysts under high temperature and reaction

Example 13 is repeated except that air (2.5 liter/hr) is used in place of the nitrogen gas and five hours in place of two hours.

Beckmann rearrangement of cyclohexanon oxime is conducted in the same manner as in Example 10 in the presence of the degraded catalyst prepared above (0.375 g). The results are shown in Table 20.

Carbonaceous materials deposited on the catalyst-are removed by combustion according to Example 10.

Recovery of catalytic activity

Regeneration treatment with ammonia water and ammonium chloride is applied once to the degraded catalyst according to Example 12, after carbonaceous materials are removed. Beckmann rearrangement of cyclohexanon oxime is carried out in the same manner as above in the presence of the regenerated catalyst. The results are shown in Table 21.

TABLE 20

| Run No. | | Reaction time elapsed (hr) | | | | | |
|---|---|---|---|---|---|---|---|
| | | 1.25 | 2.25 | 3.25 | 4.25 | 5.25 | 6.25 |
| 1 | Con. | 74.4 | 62.4 | 54.3 | 45.8 | 42.4 | 39.2 |
| | Sel. | 91.2 | 94.5 | 88.6 | 94.4 | 68.4 | 70.0 |

TABLE 21

| Run No. | | Reaction time elapsed (hr) | | | | | |
|---|---|---|---|---|---|---|---|
| | | 1.25 | 2.25 | 3.25 | 4.25 | 5.25 | 6.25 |
| 1 | Con. | 98.5 | 95.6 | 90.3 | 83.5 | 75.5 | 68.2 |
| | Sel. | 94.3 | 93.2 | 93.2 | 93.6 | 92.5 | 92.7 |

Example 15

Production of ε-caprolactam (1) The catalyst M* (1.0 g, 1.6 ml) prepared by Example 11 and packed in a reaction tube (2 cm inner diameter) made of silica glass is pre-heated at a temperature of 350° C. for one hour in a nitrogen stream (4.2 liter/hr). A mixture of cyclohexanon oxime/methanol (1/1.8 by weight) is charged at speed of 28 g/hr under WHSV=10 hr$^{-1}$ at a catalyst layer temperature of 350° C. for 6.25 hours. Product is collected every one hour under ice cooling and assayed by gas chromatography. The results are shown in Table 22.

(2) After the reaction is over, no further feeding of cyclohexanon oxime/methanol is made. A mixture of nitrogen gas (2.5 liter/hr) and air (2.5 liter/hr) is bubbled in methanol (0° C.) until methanol (3.8 vol %, 0° C. saturated concentration) is vaporized in and accompanied by nitrogen/air mixture gas. The gas is charged to the reaction tube. Temperature of the catalyst layer is raised to 430° C. The operation is conducted for 40 hours in order to remove carbonaceous materials deposited on the catalyst.

(3) Temperature is lowered to 350° C. while nitrogen is fed (4.2 liter/hr). Then, the step (1) is repeated.

(4) After the reaction is over, the step (2) above is applied to in order to remove carbonaceous materials deposited on the catalyst.

The steps (1) and (2) are conducted in series 20 times. The results are shown in Table 22.

Recovery of catalytic activity

Degraded catalyst (0.375 g) after the removal of carbonaceous materials is over is charged in a reaction tube made of stainless steel. Pre-heating is applied to at a temperature of 350° C. for one hour in a nitrogen stream (4.2 liter/hr) under an atmospheric pressure. Temperature is lowered to 200° C. and the tube is left to stand until nitrogen gas pressure reaches 8 kg/cm$^2$. After feeding of the nitrogen gas is stopped, ammonia water (28 wt %, 3.0 g/hr) is fed for three hours from the top of the reaction tube, while pressure of the catalyst layer is held at 8 kg/cm$^2$. Feeding of the ammonia water is stopped, temperature is lowered to room temperature (20° C.) under an atmospheric pressure in a nitrogen stream (4.2 liter/hr).

The catalyst (0.375 g) thus regenerated is charged in a reaction tube made of silica glass and is pre-heated at a temperature of 350° C. for one hour in a nitrogen stream (4.2 liter/hr). A mixture of cyclohexanon oxime/methanol (1/1.8 by weight) is charged at speed of 10.5 g/hr under WHSV=10 hr$^{-1}$. The results are shown in Table 23.

TABLE 22

| Run No. | | Reaction time elapsed (hr) | | | | |
|---|---|---|---|---|---|---|
| | | 1.25 | 2.25 | 3.25 | 4.25 | 5.25 | 6.25 |
| 1 | Con. | 99.6 | 97.1 | 93.2 | 89.4 | 85.3 | 80.8 |
| | Sel. | 96.5 | 95.2 | 93.3 | 94.5 | 92.6 | 93.7 |
| 20 | Con. | 56.9 | 46.2 | 39.4 | 37.0 | 33.8 | 33.4 |
| | Sel. | 91.4 | 91.3 | 92.1 | 88.0 | 85.1 | 83.4 |

TABLE 23

| Run No. | | Reaction time elapsed (hr) | | | | | |
|---|---|---|---|---|---|---|---|
| | | 1.25 | 2.25 | 3.25 | 4.25 | 5.25 | 6.25 |
| 1 | Con. | 93.7 | 90.6 | 91.3 | 88.9 | 84.9 | 82.2 |
| (21) | Sel. | 96.8 | 96.6 | 92.7 | 96.7 | 92.1 | 93.5 |

Note: Number in parenthesis: Run number serial after Table 22

Example 16

Preparation of ε-caprolactam

The catalyst M* (0.375 g, 0.6 ml) prepared by Example 11 is packed in a reaction tube. Beckmann rearrangement of cyclohexanon oxime and removal of carbonaceous materials are conducted repeatedly in the same manner as in Example 10. The results are shown in Table 24.

Recovery of catalytic activity

Degraded catalyst (0.375 g) after carbonaceous materials have been removed is charged in an autoclave and is left to stand at a temperature of 90° C. for three hours in the presence of ammonia water (28% by wt, 50 ml). The catalyst is filtered, washed with water and dried.

The catalyst thus regenerated is packed in a reaction tube and Beckmann rearrangement of cyclohexanon oxime is carried out in the same manner as above. The results are shown in Table 25.

TABLE 24

| Run No. | | Reaction time elapsed (hr) | | | | | |
|---|---|---|---|---|---|---|---|
| | | 1.25 | 2.25 | 3.25 | 4.25 | 5.25 | 6.25 |
| 1 | Con. | 98.6 | 97.2 | 96.3 | 95.4 | 94.3 | 93.1 |
| | Sel. | 99.6 | 96.7 | 96.3 | 95.9 | 95.8 | 96.6 |

TABLE 24-continued

| Run No. | | Reaction time elapsed (hr) | | | | | |
|---|---|---|---|---|---|---|---|
| | | 1.25 | 2.25 | 3.25 | 4.25 | 5.25 | 6.25 |
| 20 | Con. | 82.0 | 72.4 | 69.8 | 66.3 | 63.1 | 59.7 |
| | Sel. | 91.9 | 92.1 | 91.0 | 90.8 | 91.3 | 90.7 |

TABLE 25

| Run No. | | Reaction time elapsed (hr) | | | | | |
|---|---|---|---|---|---|---|---|
| | | 1.25 | 2.25 | 3.25 | 4.25 | 5.25 | 6.25 |
| 1 | Con. | 91.3 | 89.1 | 87.8 | 86.2 | 84.3 | 82.4 |
| (21) | Sel. | 95.9 | 94.9 | 95.8 | 94.9 | 95.2 | 95.3 |

Note Number in parenthesis: Run number serial after Table 24

Comparative Example 3

Production of ε-caprolactam and removal of carbonaceous materials are conducted using the catalyst M (0.375 g) in the same manner as in Example 10. The run is repeated 20 times. The results at the 20th run are shown in Table 26.

TABLE 26

| Run No. | | Reaction time elapsed (hr) | | | | | |
|---|---|---|---|---|---|---|---|
| | | 1.25 | 2.25 | 3.25 | 4.25 | 5.25 | 6.25 |
| 20 | Con. | 87.2 | 77.1 | 75.3 | 70.1 | 66.4 | 64.3 |
| | Sel. | 93.0 | 92.1 | 91.9 | 91.3 | 92.0 | 91.2 |

Degraded catalyst (0.375 g) after the 20th removal of carbonaceous materials is over is charged in an autoclave and is left to stand at a temperature of 90° C. for one hour in the presence of aqueous ammonium nitrate solution (7.5% by wt, 50 ml). The catalyst is filtered, washed with water and dried.

The catalyst (0.375 g) thus treated is charged again in a reaction tube of silica glass similar to that above, and production of ε-caprolactam is conducted in the same manner as above. The results at the first run, i.e., the 21st run (serial run number) are shown in Table 27.

TABLE 27

| Run No. | | Reaction time elapsed (hr) | | | | | |
|---|---|---|---|---|---|---|---|
| | | 1.25 | 2.25 | 3.25 | 4.25 | 5.25 | 6.25 |
| 1 | Con. | 81.9 | 76.7 | 71.7 | 66.6 | 60.1 | 57.0 |
| (21) | Sel. | 89.3 | 93.5 | 93.8 | 93.7 | 93.9 | 94.2 |

Note: Number in parenthesis: Run number serial after Table 26

Example 17

Beckmann rearrangement is conducted in the same manner as in Example 10 except that the catalyst O (0.375 g) prepared by Reference example 5 is used in place of the catalyst M. The results are shown in Table 28.

TABLE 28

| Run No. | | Reaction time elapsed (hr) | | |
|---|---|---|---|---|
| | | 1.25 | 3.25 | 6.25 |
| 1 | Con. | 58.1 | 44.2 | 35.6 |
| | Sel. | 70.1 | 46.2 | 40.3 |

Enforced degradation of catalysts under high temperature and reaction

The catalyst O (0.375 g, 0.6 ml) prepared by Reference example 5 is charged in a reaction tube (inner diameter=1 cm) made of silica glass. Nitrogen gas (2.5 liter/hr) is bubbled in distilled water (0° C.) until water (0.6 vol %, 0° C. saturated concentration) is vaporized in and accompanied by the nitrogen gas. The gas is charged in the reaction tube which is left to stand at a temperature of 900° C. for two hours.

After the temperature is lowered to room temperature (20° C.), Beckmann rearrangement is conducted as the same manner as in Example 10 in the presence of the catalyst (0.375 g) obtained above. The results are shown in Table 29.

TABLE 29

| Run No. | Reaction time elapsed (hr) | | |
|---|---|---|---|
| | 1.25 | 3.25 | 6.25 |
| 1 Con. | 29.0 | 17.3 | 11.2 |
| Sel. | 47.6 | 49.3 | 57.2 |

Carbonaceous materials deposited on the catalyst are removed according to Example 10.

Recovery of catalytic activity

Degraded catalyst (0.375 g) after carbonaceous materials are removed is charged in an autoclave and is left to stand at a temperature of 90° C. for one hour in the presence of ammonia water (28% by wt, 50 ml) and ammonium chloride (4 g). Then, the catalyst is filtered and charged in a flask. After hydrochloric acid (5N, 50 ml) is added, the content is stirred at a temperature of 90° C. for one hour. The catalyst is filtered, washed with water and dried.

Beckmann rearrangement is conducted in the same manner as above in the presence of the regenerated catalyst. The results are shown in Table 30.

TABLE 30

| Run No. | Reaction time elapsed (hr) | | |
|---|---|---|---|
| | 1.25 | 3.25 | 6.25 |
| 1 Con. | 79.2 | 54.2 | 48.3 |
| Sel. | 78.4 | 76.9 | 72.2 |

We claim:

1. A process for activating catalysts for production of ε-caprolactam, which comprises contacting a zeolite selected from the group consisting of pentasil crystalline silica or pentasil crystalline aluminosilicate having an Si/Al atom ratio of least 5 with either (1) an aqueous solution of ammonium salts and at least one basic material selected from ammonia, lower alkylamines, allylamines and alkylammonium hydroxides, or (2) ammonia water.

2. A process according to claim 1, wherein the lower alkylamine have the formula:

$$NR_1R_2R_3 \qquad (1)$$

wherein $R_1$, $R_2$ and $R_3$ each is a hydrogen atom or a lower alkyl group but $R_1$, $R_2$ and $R_3$ all are not hydrogen atoms.

3. A process according to claim 1, wherein the lower alkylamines have $C_{1-12}$ in the total.

4. A process according to claim 1, wherein the allylamines have $C_{3-9}$ in the total.

5. A process according to claim 1, wherein the alkylammonium hydroxides have the formula:

$$R_4R_5R_6R_7N^+ON^- \qquad (2)$$

wherein $R_4$, $R_5$, $R_6$ and $R_7$ each is a hydrogen atom, a lower alkyl group, an aralkyl group, an aryl group or an allyl group but $R_4$, $R_5$, $R_6$ and $R_7$ all are not hydrogen atoms.

6. A process according to claim 5, wherein the alkylammonium hydroxides have $C_{1-20}$ in the total.

7. A process according to claim 1, wherein the catalysts are crystalline silica or crystalline metallosilicates.

8. A process according to claim 1, wherein the contact with the aqueous solution or ammonia water is effected after activity of the catalyst is degraded.

9. A process according to claim 8, wherein the degraded catalyst is brought into contact with ammonia gas.

10. A process according to claim 1, wherein the degraded catalyst has been burned in the presence of molecular oxygen-containing gas with or without alcohols.

11. A process according to claim 1, wherein said ε-caprolactam is produced via Beckmann rearrangement reaction.

12. A process according to claim 11, wherein the contact with the aqueous solution or ammonia water is effected before the reaction of Beckmann rearrangement.

* * * * *